(12) United States Patent
Maris-Haug et al.

(10) Patent No.: US 8,518,309 B2
(45) Date of Patent: Aug. 27, 2013

(54) MEASURING DEVICE AND MEASURING METHOD FOR AN INJECTION MOLDING MACHINE FOR ASCERTAINING A BATCH-SPECIFIC CHARACTERISTIC NUMBER

(75) Inventors: Patricia Maris-Haug, Pleidelsheim (DE); Jens Ackermann, Stuttgart (DE); Stephan Geise, Ruethen (DE); Guenter Haag, Stuttgart (DE); Paeivi Lehtonen, Fellbach (DE); Philipp Liedl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 258 days.

(21) Appl. No.: 13/089,890

(22) Filed: Apr. 19, 2011

(65) Prior Publication Data

US 2011/0254183 A1 Oct. 20, 2011

(30) Foreign Application Priority Data

Apr. 20, 2010 (DE) .......................... 10 2010 027 942

(51) Int. Cl.
*B29C 45/76* (2006.01)
(52) U.S. Cl.
USPC ...................................... 264/40.1; 264/328.1
(58) Field of Classification Search
USPC ............................................ 264/40.1, 328.1
See application file for complete search history.

(56) References Cited

U.S. PATENT DOCUMENTS

| | | | | |
|---|---|---|---|---|
| 4,624,132 A * | 11/1986 | Parnaby et al. | ............. | 73/54.09 |
| 5,993,704 A * | 11/1999 | Bader | .......................... | 264/40.1 |
| 7,585,166 B2 * | 9/2009 | Buja | ............................. | 425/143 |
| 8,329,075 B2 * | 12/2012 | Bader | ......................... | 264/40.1 |

FOREIGN PATENT DOCUMENTS

| | | |
|---|---|---|
| DE | 32 11 728 | 10/1982 |
| DE | 19715630 | 4/1997 |
| EP | 482199 | 4/1991 |
| FR | 2 621 525 | 4/1989 |
| GB | 2 158 252 | 11/1985 |
| JP | 5-329864 | 12/1993 |
| JP | 11-10694 | 1/1999 |
| WO | 93/15387 | * 8/1993 |

OTHER PUBLICATIONS

Bader, C. et al., "Theologische Messungen Auf Der Spritzgiessmaschine", Kunstoffe international, Carl Hanser Verlag, Munich, 1991, vol. 81, No. 3, pp. 220-224 (with English translation of introductory paragraph).

* cited by examiner

*Primary Examiner* — Jill Heitbrink
(74) *Attorney, Agent, or Firm* — Kenyon & Kenyon LLP

(57) ABSTRACT

A measuring device for an injection molding system for ascertaining a batch-specific characteristic number of a plasticized plastic includes a flow channel which is situated between a plasticizing unit of an injection molding machine and an injection molding tool, a first pressure sensor and a second pressure sensor and a first temperature sensor and a second temperature sensor being situated along the flow channel. The flow channel has a taper between the first pressure sensor and the second pressure sensor.

4 Claims, 1 Drawing Sheet

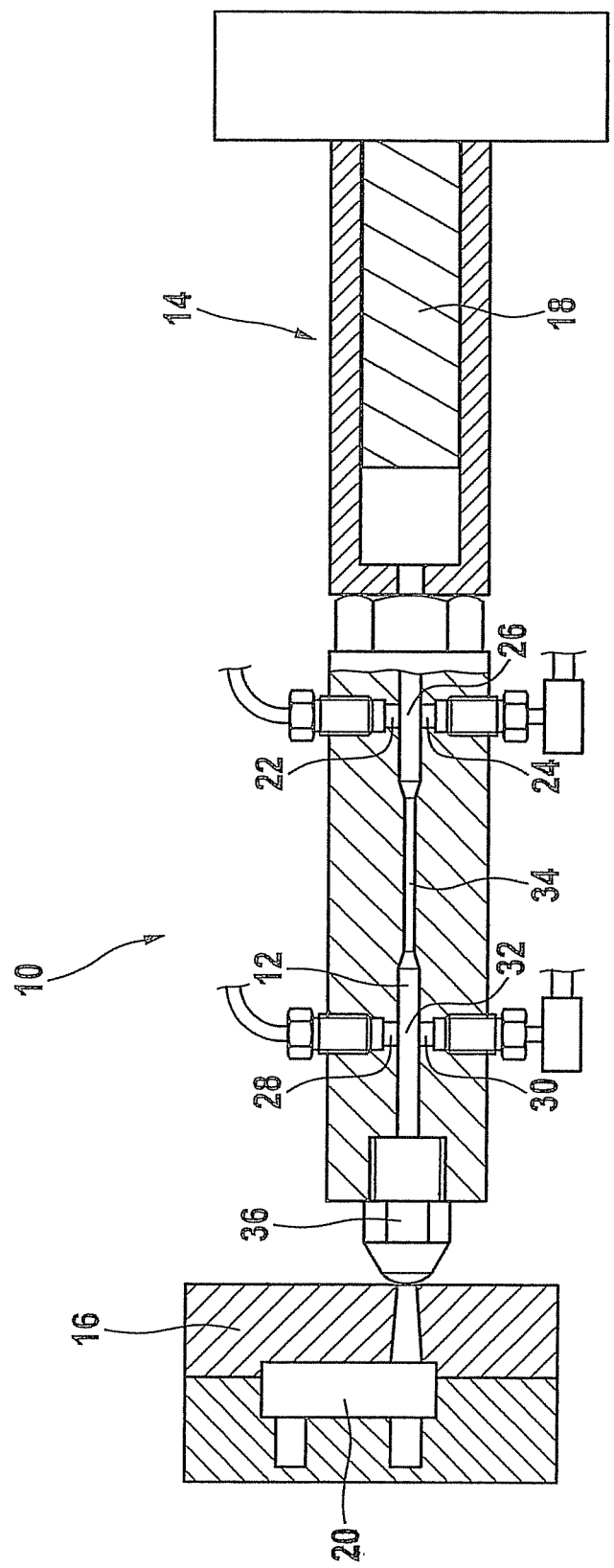

MEASURING DEVICE AND MEASURING METHOD FOR AN INJECTION MOLDING MACHINE FOR ASCERTAINING A BATCH-SPECIFIC CHARACTERISTIC NUMBER

CROSS REFERENCE

The present application claims the benefit under 35 U.S.C. §119 of German Patent Application No. DE 102010027942.0, filed on Apr. 20, 2010, which is expressly incorporated herein by reference in its entirety.

FIELD OF THE INVENTION

The present invention relates to a measuring device and a measuring method for an injection molding machine for ascertaining a batch-specific characteristic number during an injection molding operation.

BACKGROUND INFORMATION

There are numerous devices and methods for ascertaining characteristics of materials used in injection molding processes. For example, a device and a method for determining rheological material data of polymers are described in German Patent Application No. DE 197 15 630 A1, the device being provided for coupling, for example, to an extruder. The device has a flow channel in a housing which is used as the measuring section, pressure and temperature sensors being provided in the area of the measuring section, the device having an outlet nozzle at the free end of the measuring section, a heating element which heats the flow channel and a temperature control device, the temperature control device controlling a heating and cooling circuit which has a fluid heat transfer medium, the diameter of the flow channel between the inlet opening of the flow channel and the outlet nozzle having a uniform diameter. The method is used to control heat transfer with the goal of increasing the process stability of the injection molding process.

The disadvantage of devices and methods of this type is that ascertaining material-dependent data is complex and produces inaccurate results.

SUMMARY

An object of the present invention is to provide a measuring device for an injection molding machine and a measuring method for ascertaining a batch-specific characteristic number of a plasticized plastic which enable(s) easier ascertainment of material-dependent data and in which the accuracy of the material-dependent data is improved.

The example measuring device according to the present invention for an injection molding system for ascertaining a batch-specific characteristic number of a plasticized plastic includes a flow channel which is situated between a plasticizing unit of an injection molding machine and an injection molding tool, a first pressure sensor and a second pressure sensor and a first temperature sensor and a second temperature sensor being situated along the flow channel. According to the example embodiment of the present invention, the flow channel has a taper between the first pressure sensor and the second pressure sensor.

A plasticizing screw for plasticizing a plastic is preferably situated within the plasticizing unit of the injection molding machine. The flow channel of the measuring device according to the present invention preferably extends from the end of the plasticizing screw pointing in the direction of the injection molding tool, penetrates the injection molding tool, and empties into a cavity formed within the injection molding tool. The flow channel is connected to the plasticizing unit of the injection molding machine in such a way that, for example, plasticized plastic may flow out of the plasticizing unit, through the flow channel, and into the cavity of the injection molding tool with the aid of the plasticizing screw. The flow channel has a first pressure sensor and a second pressure sensor, the pressure sensors each being able to carry out a measurement of the pressure, for example the mass pressure, of the plasticized plastic flowing through the flow channel. The first pressure sensor may be situated on a section of the flow channel the plasticizing unit, and the second pressure sensor may be situated on a section of the flow channel the injection molding tool. The pressure sensors, which may be situated along a geometric center line of the flow channel, each form a first measuring point and a second measuring point. The distance between the first pressure sensor and the second pressure sensor, or between the first measuring point and the second measuring point, corresponds to a measuring section along the flow channel for measuring a pressure difference. In addition, a first temperature sensor may be situated at the first measuring point, and a second temperature sensor may be situated at the second measuring point. The temperature sensors may be designed in the form of infrared sensors. The flow channel has a taper between the first pressure sensor and the second pressure sensor. The taper may be designed in such a way that the diameter of the flow channel in the area of the taper is reduced in the radial direction of the flow channel. This taper results in a greater pressure difference between the pressure sensors, so that even small changes in the plasticized plastic may be detected and evaluated. The flow channel may have a diameter of the same size or a diameter of different sizes upstream and downstream from the taper in the flow direction, for example in the direction in which the plasticized plastic flows from the plasticizing screw or plasticizing unit toward the cavity. The taper may be designed, for example, in the form of an injection nozzle. However, it is also possible to design the taper separately, i.e., not using an existing component, within the flow channel by reducing the diameter of the flow channel. Reducing the flow cross section of the flow channel at the taper causes the pressure to increase in the plasticized plastic flowing through the flow channel. A pressure difference in the plasticized plastic which is flowing through the flow channel may be measured by taking pressure measurements at the first measuring point and the second measuring point. For example, the viscosity of the plasticized plastic flowing through the flow channel may be detected by measuring the pressure difference and the temperature of the plasticized plastic. Situating the measuring device between the plasticizing unit and the injection molding tool makes it possible to carry out pressure measurements at the first measuring point and at the second measuring point at defined points in time and/or at defined time intervals during an injection operation. The ascertainment of the pressure measured values and, for example, the material-dependent data derived therefrom, may be simplified due to the fact that the plasticized plastic flows through the flow channel and thus through the measuring device, preferably during an injection operation common in production without process changes. Furthermore, the measuring device according to the present invention makes it possible to carry out pressure measurements, for example, in directly consecutive injection operations. This enables the number of measurements carried out, for example, for a certain plastic, to be increased, which may improve the accuracy of the ascertained material-dependent data.

In one preferred embodiment of the measuring device, the first pressure sensor is situated within the injection molding machine and/or the second pressure sensor is situated within the injection molding tool. The first pressure sensor may be designed as an internal injection molding machine pressure sensor which may be designed, for example, as a hydraulic pressure sensor or an injection pressure sensor. The pressure sensor integrated into the injection molding machine may be used to detect the pressure of the plasticized plastic, it being possible to use the measured pressure during ascertainment of the pressure difference as the pressure of the first measuring point. The second pressure sensor may be, for example, a pressure sensor which is situated, for example, in the injection molding tool and which may be situated, for example, along the flow channel within the injection molding tool. The first pressure sensor is preferably situated upstream from the taper in the flow direction, and the second pressure sensor is preferably situated downstream from the taper in the flow direction. The use of existing pressure sensors in the injection molding machine or in the injection molding tool makes it possible to simplify the construction of the measuring device and lower the costs of the measuring device. However, it is also possible to situate the first pressure sensor and the second pressure sensor along the flow channel in the injection molding machine, or to situate the first pressure sensor and the second pressure sensor along the flow channel in the injection molding tool.

In one particularly preferred specific embodiment, the measuring device is designed as a separate component. By designing the measuring device according to the present invention as a separate component, the measuring device may be situated between the injection nozzle of the injection molding machine and the plasticizing unit of the injection molding machine. This makes it possible to easily integrate the measuring device into an injection molding system and it also simplifies maintenance of the measuring device, since the measuring device may be removed as a single component and replaced, for example, with another measuring device.

In one preferred specific embodiment, a first external evaluation module and a second external evaluation module are provided. The first external evaluation module is used to ascertain the measuring times, for example the beginning and the end of a pressure measurement or the duration of the measurement, as a function of the pressures measured at the first and second measuring points. The measuring times and/or the measuring duration may also be set manually. The pressures ascertained at the first and second measuring points are evaluable in the second external evaluation module. This makes it possible to ascertain material-dependent data, for example the viscosity of the plasticized plastic.

In one further preferred specific embodiment, the first evaluation module and/or the second evaluation module is/are integrated into a control system and/or regulating system of the injection molding machine. Due to the fact that at least one evaluation module is integratable into the control system and/or regulating system of the injection molding machine, the costs of the measuring device according to the present invention may be reduced. Furthermore, the measuring operation may be optimally adjusted to the parameters predefined by the control system and/or regulating system of the injection molding machine with the aid of the measuring device.

The present invention furthermore relates to an injection molding system which includes at least one measuring device designed and refined as described above. The injection molding system includes an injection molding machine which has a plasticizing unit and an injection nozzle as well as an injection molding tool adjacent to the injection molding machine, the injection molding machine being connected to the injection molding tool via its injection nozzle.

The present invention furthermore relates to a measuring method for ascertaining a batch-specific characteristic number of a plasticized plastic while the plastic is flowing through a flow channel, which is situated between a plasticizing unit and an injection molding tool and which has a taper, during an injection molding operation, an example method includes the following steps:

carrying out a first measurement during a first injection molding operation, in which first measured data of a first pressure sensor provided along the flow channel and first measured data of a second pressure sensor provided along the flow channel are detected during a first measurement interval having a first lower measuring time and a first upper measuring time;

forwarding the first measured data of the first measurement to a first evaluation module and to a second evaluation module;

calculating a second measurement interval in the first evaluation module at a second lower measuring time and at a second upper measuring time;

ascertaining a first batch-specific characteristic number in the second evaluation module;

storing the first lower and upper measuring times and the first batch-specific characteristic number;

carrying out a second measurement during a second injection molding operation, in which second measured data of the first pressure sensor and of the second pressure sensor are detected during the second measurement interval.

The example measuring method according to the present invention makes it possible to ascertain a characteristic number for a batch of plasticized plastic during an injection molding operation, providing specific material properties without making it necessary to take samples or carry out a separate evaluation to determine the material properties in a laboratory. The abstract characteristic number is batch-specific and reproducible, the characteristic number being ascertained by the measuring method according to the present invention independently of the process parameters. The batch-specific characteristic number is generally dependent on the temperature. Consequently, the temperature values of the plasticized plastic ascertained via the temperature sensors are incorporated into the calculation of the batch-specific characteristic number. A first measurement is carried out during a first measurement interval during a first injection molding operation, the first measurement interval beginning at a first lower measuring time and ending at a first upper measuring time. During the first measurement interval, first measured data of the first pressure sensor and of the second pressure sensor and of the first temperature sensor and of the second temperature sensor are detected for the plasticized plastic flowing through the flow channel. The pressure sensors may detect, for example, the mass pressure of the plasticized plastic.

The first measured data detected in a first measurement are forwarded to a first evaluation module and to a second evaluation module. The measured data may be forwarded during a measurement interval or after a measurement interval has ended.

In the first evaluation module, a second measurement interval having a second lower measuring time and a second upper measuring time is adaptively calculated with the aid of an algorithm on the basis of the first measured data detected by the pressure sensors and provided by the first pressure sensor and the second pressure sensor and the first temperature sensor and the second temperature sensor. The second or further lower and upper measuring times are calculated adaptively or adapted to the measured data which are detected during injection molding operations and which may vary from material to material and from batch to batch. The measurement interval calculated in the first evaluation module, for example, the second measurement interval, covers the time period within the injection molding operation in which a laminar flow in the measuring device and/or the flow channel may be assumed. The lower measuring time marks the start of the laminar flow in the measuring device, and the upper measuring time marks the end of the operation for filling the cavity with the plasticizing plastic, which is indicated by the buildup in counterpressure, the laminar flow ending at this measuring time. The calculation of the second measurement interval in the first evaluation module takes into account, among other things, the injection molding parameters, for example the injection rate as well as the dependence of the viscosity of the plasticized plastic on the shear rate.

The first batch-specific characteristic number is ascertained in the second evaluation module. The batch-specific characteristic number for the relevant plasticized plastic is ascertained on the basis of the first measured data detected by the pressure sensors and the temperature sensors and the pressure time curve of the measured data of the first pressure sensor and the second pressure sensor. To ascertain the first batch-specific characteristic number, the pressure difference detected between the first pressure sensor and the second pressure sensor is evaluated and filtered, the batch-specific characteristic number being formed from the quotient of the pressure difference and the inflow velocity of the plasticized plastic. Statistical evaluation methods are used to average the measured data ascertained with the aid of the pressure sensors and the temperature sensors, so that the statistical significance of the batch-specific characteristic number may be considerably increased.

The first lower and upper measuring times as well as the first batch-specific characteristic number are stored.

A second measurement is carried out during a second injection molding operation following the first injection molding operation, whereby the second injection molding operation having the second measurement does not need to directly follow the first injection molding operation. The second measurement is carried out in the calculated second measurement interval, starting at the lower measuring time and ending at the second upper measuring time. The second measured data detected by the first pressure sensor and the second pressure sensor and the first temperature sensor and the second temperature sensor are forwarded to the first and second evaluation modules, where another evaluation is carried out.

The measurement may be repeated any number of times after the second measurement, so that n measurements are possible, n measurement intervals having n lower measuring times and n upper measuring times being possible to obtain n measured data.

Due to the example measuring method according to the present invention, the ascertainment of a batch-specific characteristic number during the injection molding operation without taking samples is made possible and thus substantially simplified. This makes it possible to directly evaluate the plasticized plastic used during an injection molding operation, which enables fluctuations in the material quality of the plasticized plastic to be detected immediately. Integrating the measuring method into the injection molding operation permits a number of directly consecutive measuring operations to be carried out, which increases the accuracy of the measurement results.

Preferably, the first lower measuring time and/or the first upper measuring time is/are set manually, and/or the second lower measuring time and/or the second upper measuring time is/are set manually. Due to the possibility of manually setting, for example, the first lower measuring time and the first upper measuring time, existing empirical values for the same or a similar plastic which are to be used in the injection molding operation may be taken into account. This may shorten the amount of time that passes before ascertaining, for example, the suitable measurement intervals during which a laminar flow may be assumed, so that less rejects are produced.

In a particularly preferred manner, the lower measuring times and/or the upper measuring times are statistically evaluated, and the values ascertained for the subsequent injection molding operations are used for the lower measuring time and/or the upper measuring time. By storing and statistically evaluating the lower and/or upper measuring times, for example in the form of a calculation of mean values, and by providing the evaluated data for ascertaining the measurement intervals and measuring times for subsequent injection molding operations, it is possible to speed up the ascertainment of the optimum measuring times for a batch of plasticized plastic, since the statistically ascertained measuring times used for ascertainment lie close to the batch-specific measuring times. As a result, the learning process for ascertaining the batch-specific measuring times may be carried out within just a few injection molding operations, and the production of rejects may thus be reduced. Furthermore, the measuring times ascertained within a learning cycle may be statistically detected and evaluated, for example by forming an average lower measuring time and/or an average upper measuring time. The averaged lower and/or upper measuring times may be manually or automatically fixed for the batch of plastic to be processed after a preset number of injection molding operations, and they may be ascertained again only after using another batch of plastic in a new learning process, triggered, for example, by a manual signal or by a change in the ascertained batch characteristic number.

In a particularly preferred manner, the batch-specific characteristic number ascertained in the second evaluation module is supplied to a control system and/or regulating system of an injection molding machine in the form of an input signal. Ascertained material fluctuations may thus be taken into account by the control system and/or regulating system of the injection molding machine, and a fluctuation in process quality may be avoided. In addition, possible material mix-ups during processing may be detected at an early point, which may reduce the error rate in the injection molding operation.

BRIEF DESCRIPTION OF THE DRAWINGS

The present invention is explained in greater detail below on the basis of preferred exemplary embodiments, with reference to the Figure.

FIG. 1 shows a schematic view of an example measuring device according to the present invention.

DETAILED DESCRIPTION OF EXAMPLE EMBODIMENTS

Measuring device 10 illustrated schematically in FIG. 1 has a flow channel 12, which is situated between a plasticizing unit 14 of an injection molding machine and an injection molding tool 16. Flow channel 12 is connected to plasticizing unit 14, in which a plasticizing screw 18 is situated for plasticizing a plastic, in such a way that the plasticized plastic may flow from plasticizing unit 14 through flow channel 12 to a cavity 20 which is formed inside injection molding tool 16.

Flow channel 12 has a first pressure sensor 22 and a first temperature sensor 24 on a first section plasticizing unit 14, the sensors being situated at a first measuring point 26. First pressure sensor 22 may measure the mass pressure of the plasticized plastic flowing through flow channel 12, for example, at first measuring point 26, first temperature sensor 24, for example an infrared sensor, being able to detect the temperature of the plasticized plastic.

A second pressure sensor 28 and a second temperature sensor 30 are situated at a second measuring point 32 on a second section of flow channel 12 injection molding tool 16.

A taper 34, through which the plasticized plastic flows, is formed between first measuring points 26 and second measuring point 32 in flow channel 12. As shown in FIG. 1, flow channel 12 preferably has the same diameter at both its first measuring point 26 and at its second measuring point 32. Taper 34 itself has a diameter of flow channel 12 which is reduced compared to first measuring point 26 and second measuring point 32. Due to taper 34, a change in pressure forms in the plasticized plastic flowing through flow channel 12, the pressure difference being ascertainable by comparing the pressure measurements at first measuring point 26 and at second measuring point 32. The viscosity of the plasticized plastic may be ascertained, and a batch-specific characteristic number derived from the ascertained pressure difference, the geometry of the measuring device, and the temperature ascertained via the temperature sensors.

An injection nozzle 36, via which the plasticized plastic is injected from the injection molding machine into cavity 20 of injection molding tool 16, is provided along flow channel 12.

In the specific embodiment illustrated here, both first pressure sensor 22 and second pressure sensor 28 are situated within the injection molding machine, first pressure sensor 22 and second pressure sensor 28 being situated along flow channel 12 between plasticizing unit 14 and injection nozzle 36 of the injection molding machine.

What is claimed is:

1. A measuring method for ascertaining a batch-specific characteristic number of a plasticized plastic, while plastic flows through a flow channel, which is situated between a plasticizing unit and a tool, the flow channel having a taper, during an injection molding operation, the method comprising:
    carrying out a first measurement during a first injection molding operation, in which first measured data of a first pressure sensor provided along the flow channel and first measured data of a second pressure sensor provided along the flow channel are detected during a first measurement interval having a first lower measuring time and a first upper measuring time;
    forwarding the first measured data of the first measurement to a first evaluation module and to a second evaluation module;
    calculating a second measurement interval in the first evaluation module at a second, lower measuring time and at a second, upper measuring time;
    ascertaining a first batch-specific characteristic number in the second evaluation module;
    storing the first lower and upper measuring times and the first batch-specific characteristic number; and
    carrying out a second measurement during a second injection molding operation, in which second measured data of the first pressure sensor and of the second pressure sensor are detected during the second measurement interval.

2. The measuring method as recited in claim 1, wherein at least one of the first lower measuring time, the first upper measuring time, the second lower measuring time, and the second upper measuring time is set manually.

3. The measuring method as recited in claim 1, wherein at least one of the lower and upper measuring times are statistically evaluated, and values ascertained for subsequent injection molding operations are used for at least one of the lower and the upper measuring time.

4. The measuring method as recited in claim 1, wherein the batch-specific characteristic number ascertained in the second evaluation module is supplied to at least one of a control system and a regulating system of an injection molding machine in the form of an input signal.

* * * * *